United States Patent
Condon et al.

(10) Patent No.: US 12,266,432 B2
(45) Date of Patent: Apr. 1, 2025

(54) SYSTEM AND METHOD FOR CLAIMS MEDICAL RECORD AUTOMATION

(71) Applicant: HARTFORD FIRE INSURANCE COMPANY, Hartford, CT (US)

(72) Inventors: Holly Sebrell Condon, West Suffield, CT (US); Jennifer Patrice Ing Farnum, West Sacramento, CA (US); Nise Junior Kuriakose, South Windsor, CT (US); Gary S. Tomchik, Houston, TX (US); Shaun Andrew Youngberg, Castle Rock, CO (US); Michael Zaerr, Westfield, IN (US)

(73) Assignee: HARTFORD FIRE INSURANCE COMPANY, Hartford, CT (US)

(*) Notice: Subject to any disclaimer, the term of this patent is extended or adjusted under 35 U.S.C. 154(b) by 230 days.

(21) Appl. No.: 18/065,811

(22) Filed: Dec. 14, 2022

(65) Prior Publication Data
US 2024/0203544 A1 Jun. 20, 2024

(51) Int. Cl.
- G06F 16/22 (2019.01)
- G06Q 10/10 (2023.01)
- G16H 10/20 (2018.01)
- G16H 10/60 (2018.01)

(52) U.S. Cl.
CPC ............. *G16H 10/60* (2018.01); *G06Q 10/10* (2013.01)

(58) Field of Classification Search
CPC ................................ G16H 10/60; G06Q 10/10
See application file for complete search history.

(56) References Cited

U.S. PATENT DOCUMENTS

| | | | |
|---|---|---|---|
| 10,276,263 B2 | 4/2019 | Connely, IV et al. | |
| 11,049,235 B2 | 6/2021 | Wheaton et al. | |
| 11,443,416 B2 | 9/2022 | Liao et al. | |
| 2003/0069759 A1 | 4/2003 | Smith | |
| 2015/0039334 A1 | 2/2015 | de Traversay et al. | |
| 2018/0121843 A1 | 5/2018 | Connely, IV et al. | |
| 2019/0156921 A1* | 5/2019 | Kohli | G06F 16/93 |
| 2020/0278999 A1 | 9/2020 | Mukherji et al. | |
| 2022/0291949 A1 | 9/2022 | Blohm et al. | |
| 2024/0086384 A1* | 3/2024 | Soon-Shiong | G06F 16/2255 |

* cited by examiner

*Primary Examiner* — Maroun P Kanaan
(74) *Attorney, Agent, or Firm* — Buckley, Maschoff & Talwalkar LLC (57) ABSTRACT

A system may include an incoming image document data store containing electronic records. Each record may include an image document identifier and an image file along with associated optical character recognition and natural language processing information generated by a cloud-based computing environment. An incoming image document tool receives, from a remote user device, an indication of a selected image document. The tool may then retrieve information about the selected image document and automatically map at least some of the associated optical character recognition and natural language processing information to pre-determined document data fields. The tool may display the mapped information and receive an indication of acceptance. The mapped information and image file may then be stored in an enterprise data store and a workflow may be automatically assigned to the selected image document in accordance with the mapped information and enterprise logic.

21 Claims, 12 Drawing Sheets

| MEDICAL IMAGE ID 1002 | IMAGE NAME 1004 | OCR/NLP DATA 1006 | MAPPING DATA 1008 | ASSIGNED WORKFLOW 1010 |
|---|---|---|---|---|
| MI_101 | CLAIM_12345.01 | OCR.TXT | | WF_101 |
| MI_102 | MS._WEST_05/05/2025 | Link | | NO REVIEW |
| MI_103 | Image Link | Dictionary | | FOLLOW-UP |
| MI_104 | CLAIM54321.02 | Metadata | | REVIEW |

SYSTEM AND METHOD FOR CLAIMS MEDICAL RECORD AUTOMATION

BACKGROUND

In some cases, an enterprise may process image documents. For example, an insurer might process thousands of incoming medical documents (e.g., doctor reports, hospital records, etc.) on a daily basis or several millions of records per year. Typically, an employee—such as a claim adjuster—manually reviews each document and enters the relevant information into an enterprise system. For example, a date of treatment and provider name associated with a medical document might be located by the employee and entered into an enterprise database. The enterprise database may then be used to further process the document (e.g., by scoring a document, assigning a workflow, etc.). Such an approach, however, can be a time consuming and error prone process—especially when a substantial number of image documents and/or various types of relevant information are involved.

Systems and methods for improvements in processes relating to the management of image documents, including image document scoring, while avoiding unnecessary burdens on computer processing resource utilization, would be desirable.

SUMMARY OF THE INVENTION

According to some embodiments, systems, methods, apparatus, computer program code and means may provide ways to facilitate management of image documents. For example, a system may include an incoming image document data store containing electronic records. Each record may include an image document identifier and an image file along with associated optical character recognition and natural language processing information generated by a cloud-based computing environment. An incoming image document tool receives, from a remote user device, an indication of a selected image document. The tool may then retrieve information about the selected image document and automatically map at least some of the associated optical character recognition and natural language processing information to pre-determined document data fields. The tool may display the mapped information and receive an indication of acceptance. The mapped information and image file may then be stored in an enterprise data store and a workflow may be automatically assigned to the selected image document in accordance with the mapped information and enterprise logic.

Some embodiments provide means for receiving, by a computer processor of an incoming image document tool from a user of a remote user device via a distributed communication network, an indication of a selected image document; means for retrieving, from an incoming image document data store, information about the selected image document, wherein the incoming image document data store contains electronic records, each record including an image document identifier and an image file along with associated optical character recognition and natural language processing information generated by a cloud-based computing environment for an enterprise; based on the retrieved information, means for automatically mapping at least some of the associated optical character recognition and natural language processing information for the selected image document to pre-determined document data fields; means for displaying the mapped information via the remote user device; means for receiving, from the remote user device, an indication of acceptance of the mapped information; responsive to the received indication of acceptance, means for storing the mapped information and image file in an enterprise data store; and means for automatically assigning a workflow to the selected image document in accordance with the mapped information and enterprise logic A technical effect of some embodiments of the invention is an improved and computerized method of managing and scoring image documents for an enterprise. With these and other advantages and features that will become hereinafter apparent, a more complete understanding of the nature of the invention can be obtained by referring to the following detailed description and to the drawings appended hereto.

DESCRIPTION

Before the various exemplary embodiments are described in further detail, it is to be understood that the present invention is not limited to the particular embodiments described. It is also to be understood that the terminology used herein is for the purpose of describing particular embodiments only and is not intended to limit the scope of the claims of the present invention.

In the drawings, like reference numerals refer to like features of the systems and methods of the present invention. Accordingly, although certain descriptions may refer only to certain figures and reference numerals, it should be understood that such descriptions might be equally applicable to like reference numerals in other figures.

The present invention provides significant technical improvements to facilitate data availability, consistency, and analytics associated with image documents. The present invention is directed to more than merely a computer implementation of a routine or conventional activity previously known in the industry as it provides a specific advancement in the area of electronic record availability, consistency, and analysis by providing improvements in the operation of a computer system that uses machine learning and/or predictive models to ensure data quality. The present invention provides improvement beyond a mere generic computer implementation as it involves the novel ordered combination of system elements and processes to provide improvements in the speed at which such data can be made available and consistent results. Some embodiments of the present invention are directed to a system adapted to automatically validate information, analyze electronic records, aggregate data from multiple sources including text mining, determine appropriate document scores and workflows, etc. Moreover, communication links and messages may be automatically established (e.g., to provide image document reports and alerts to appropriate parties within an organization), aggregated, formatted, exchanged, etc. to improve network performance (e.g., by reducing an amount of network messaging bandwidth and/or storage required to support incoming image document collection, analysis, and distribution).

Figure 1:
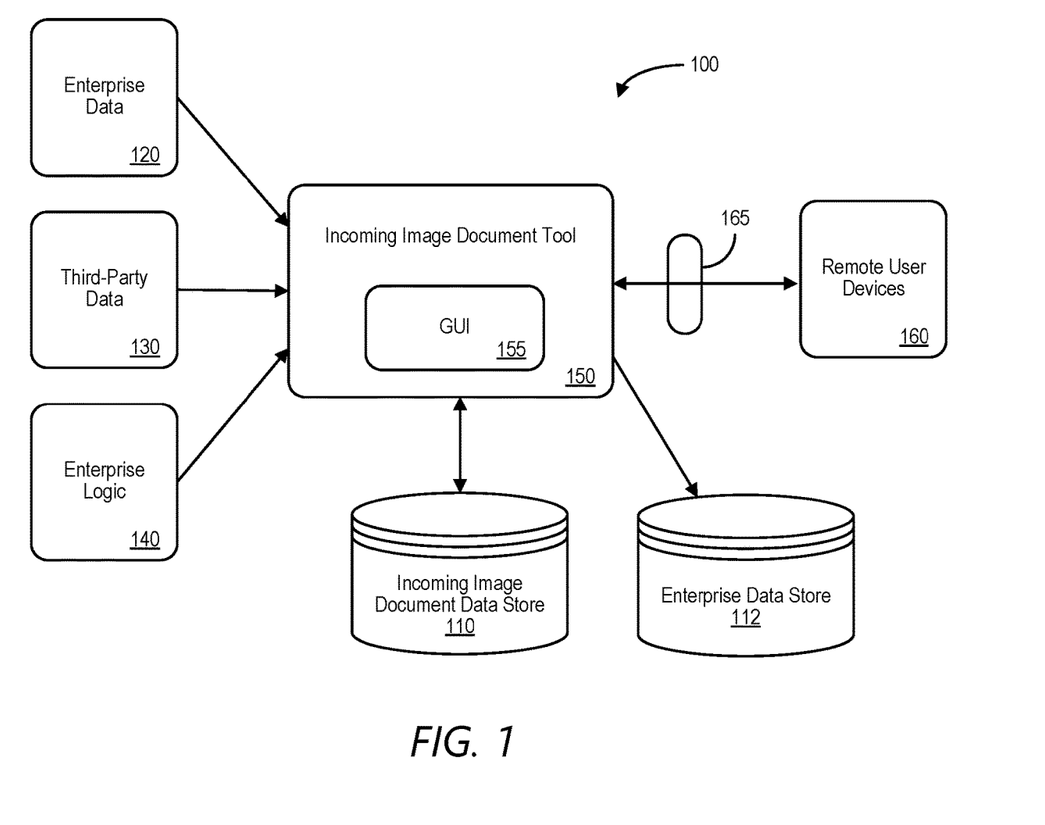
FIG. 1 is block diagram of a system in accordance with to some embodiments of the present invention.

FIG. 1 is a high-level block diagram of a system 100 according to some embodiments of the present invention. In particular, the system 100 includes an incoming image document tool 150 that may access information in an incoming image document data store 110 (e.g., storing a set of electronic records representing medical documents, each record including, for example, one or more document identifiers, images, cloud-generated results, etc.) and/or an enterprise data store 112 (e.g., to store automatically mapped image information). The incoming image document tool 150 may also retrieve information from other data stores or sources (e.g., enterprise data 120 about existing insurance policies and insurance claims, third-party data 130 such as police reports, Department of Motor Vehicle records, etc., and enterprise logic 140 defining how documents should be routed or evaluated) in connection with a Graphical User Interface ("GUI") 155 and apply machine learning or artificial intelligence algorithms and/or models to the electronic records. The incoming image document tool 150 may also exchange information with remote user devices 160 (e.g., via communication port 165 that might include a firewall). According to some embodiments, GUI 155 of the incoming image document tool 150 may facilitate the display of information associated with incoming documents via one or more remote computers (e.g., to enable a manual review of automatically generated image document tags, establish a communication link with a claim analyst or handler, and/or initiate an automatically assigned workflow) and/or the remote user devices 160 (e.g., associated with a claim adjuster). For example, the remote user devices 160 may receive updated information (e.g., new document tags) from the incoming image document tool 150. Based on the updated information, a user may review the data from the incoming image document data store 110 and make informed decisions about image document management. Note that the incoming image document tool 150 and/or any of the other devices and methods described herein might be associated with a cloud-based environment and/or a third-party, such as a vendor that performs a service for an enterprise.

The incoming image document tool 150 and/or the other elements of the system 100 might be, for example, associated with a Personal Computer ("PC"), laptop computer, smartphone, an enterprise server, a server farm, and/or a data store or similar storage devices. According to some embodiments, an "automated" incoming image document tool 150 (and/or other elements of the system 100) may facilitate updates of electronic records in the incoming image document data store 110. As used herein, the term "automated" may refer to, for example, actions that can be performed with little (or no) intervention by a human.

As used herein, devices, including those associated with the incoming image document tool 150 and any other device described herein may exchange information via any communication network which may be one or more of a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

The incoming image document tool 150 may store information into and/or retrieve information from the incoming image document data store 110. The incoming image document data store 110 might, for example, store electronic records representing a plurality of incoming image documents, each electronic record having a model identifier and an image file. The incoming image document data store 110 may also contain information about prior and current interactions with entities, including those associated with the remote devices 160. The incoming image document data store 110 may be locally stored or reside remote from the incoming image document tool 150. As will be described further below, the incoming image document data store 110 may be used by the incoming image document tool 150 in connection with an interactive user interface to provide information about image document management. Although a single incoming image document tool 150 is shown in FIG. 1, any number of such devices may be included. Moreover, various devices described herein might be combined according to embodiments of the present invention.

Figure 2:
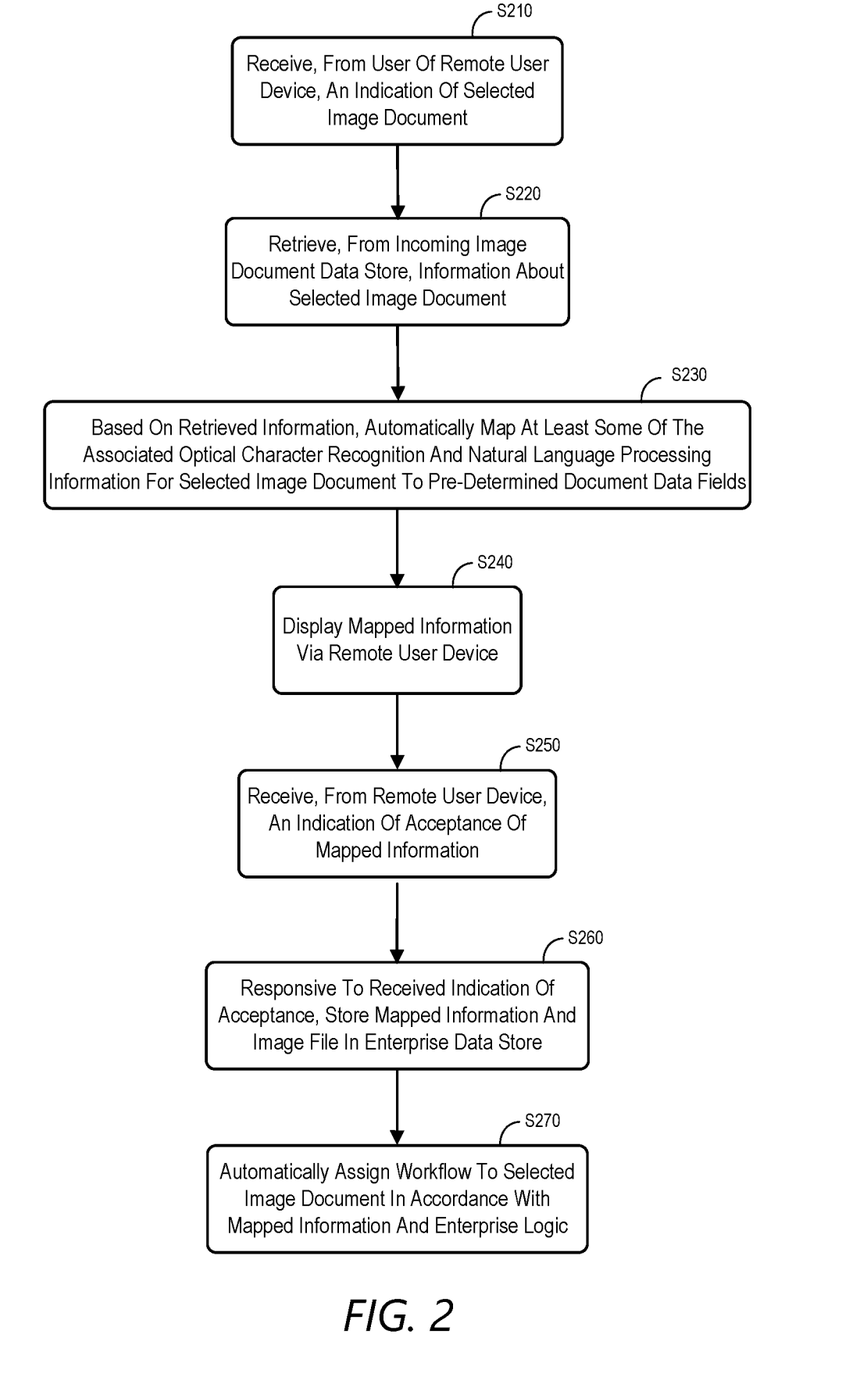
FIG. 2 illustrates a method according to some embodiments of the present invention.

FIG. 2 illustrates a method that might be performed, for example, by some or all of the elements of the system 100 described with respect to FIG. 1 according to some embodiments of the present invention. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At S210, a computer processor of an incoming image document tool may receive, from a user of a remote user device via a distributed communication network, an indication of a selected image document. For example, a user may select a particular image document from a list of available image documents, search for a particular image document, etc. The image document might comprise, for example, a Portable Document Format ("PDF") file, a bitmap ("BMP") image, etc. The image documents might comprise, for example, medical records that are received via electronic mail, a facsimile machine, a scanner device, etc. At S220, the system may retrieve, from an incoming image document data store, information about the selected image document. The incoming image document data store may, according to some embodiments, contain electronic records, each record including an image document identifier and an image file along with associated optical character recognition and natural language processing information generated by a cloud-based computing environment for the enterprise.

As used herein, the phrase "optical character recognition" may refer to, for example, the conversion of images of typed (e.g., including various fonts), handwritten, or printed text into machine-encoded text (e.g., an ASCII text ("TXT") file). Moreover, the phrase "natural language processing" may refer to, for example, a process to analyze large amounts of natural language data to understand the contents of images, including contextual nuances, to accurately extract information and insights contained in the images. According to some embodiments, the associated optical character recognition and natural language processing information is represented by a JavaScript Object Notation ("JSON") file.

Based on the retrieved information, at S230 the system may automatically map at least some of the associated optical character recognition and natural language processing information for the selected image document to pre-determined document data fields. At S240, the mapped information may be displayed via the remote user device and the system may receive, from the remote user device, an indication of acceptance of the mapped information at S250. Responsive to the received indication of acceptance, the system may store the mapped information and image file in an enterprise data store at S260. According to some embodiments, the indication of acceptance of the mapped information includes in some cases at least one adjustment to the mapped information (e.g., a medical provider field might be corrected from "Dr. Jonez" to "Dr. Jones"). In other cases, no adjustment to the mapped information might be made.

At S270, the system may automatically assign a workflow for the selected image document in accordance with the mapped information and enterprise logic. For example, the incoming image files might comprise medical records, the enterprise might be an insurer, and the assigned workflow may represent associated with insurance claim processing. The enterprise logic might be associated a risk score, a volatility score, a predicted recovery time, etc. Note that insurance claim processing might be associated with workers' compensation insurance, group benefit insurance, short term disability insurance, long term disability insurance, automobile insurance, general liability insurance, etc. Moreover, the pre-determined document data fields might include an insurance policy identifier, a patient name, a patient date of birth, a medical provider identifier, an injury description, a medical treatment date, medical treatment information, etc. Other examples of data fields might include an insurance claim identifier and claim demographic information (e.g., a disability status, a claim status, etc.). Note that according to some embodiments, the mapped information is further processed by Machine Learning ("ML") model (e.g., trained using image data along with appropriate tags), an automated data analysis algorithm, and/or a symbolic rules model (e.g., explicitly defined by an expert).

Figure 3:
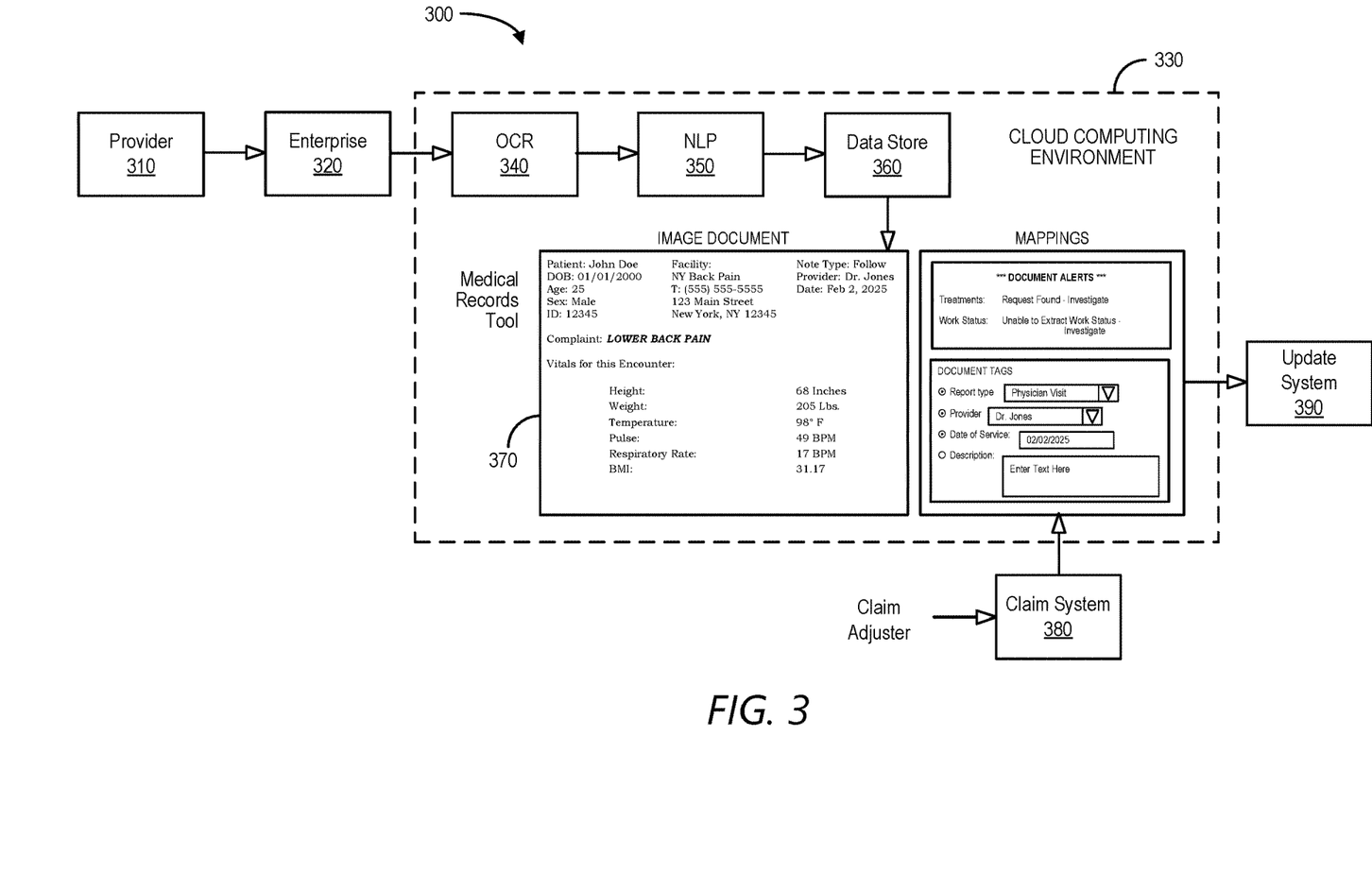
FIG. 3 is a medical record image high level flow in accordance with some embodiments.

FIG. 3 is a medical record image high level flow 300 in accordance with some embodiments. A provider 310 may send a medical record image to an enterprise 320 (e.g., an insurer) that forwards the image to a cloud computing environment 330 (e.g., an AMAZON® Web Services ("AWS") computing environment). The cloud computing environment 330 may execute Optical Character Recognition ("OCR") 340 and Natural Language Processing ("NLP") 350 to create medical record data in a data store 360 along with the medical image. Information in the data store 360 can then be displayed via a medical record tool 370 to be reviewed by a claim adjuster directly or via a claim system 380. Although a claim adjuster is used herein by way of example, note that embodiments may be associated with any other type of user (including a claim supervisor, a nurse, a claim manager, an attorney, etc.). When approved, the medical record data may be used to notify or update a system 390 (e.g., to determine an appropriate workflow for the medical record image).

Figure 4:
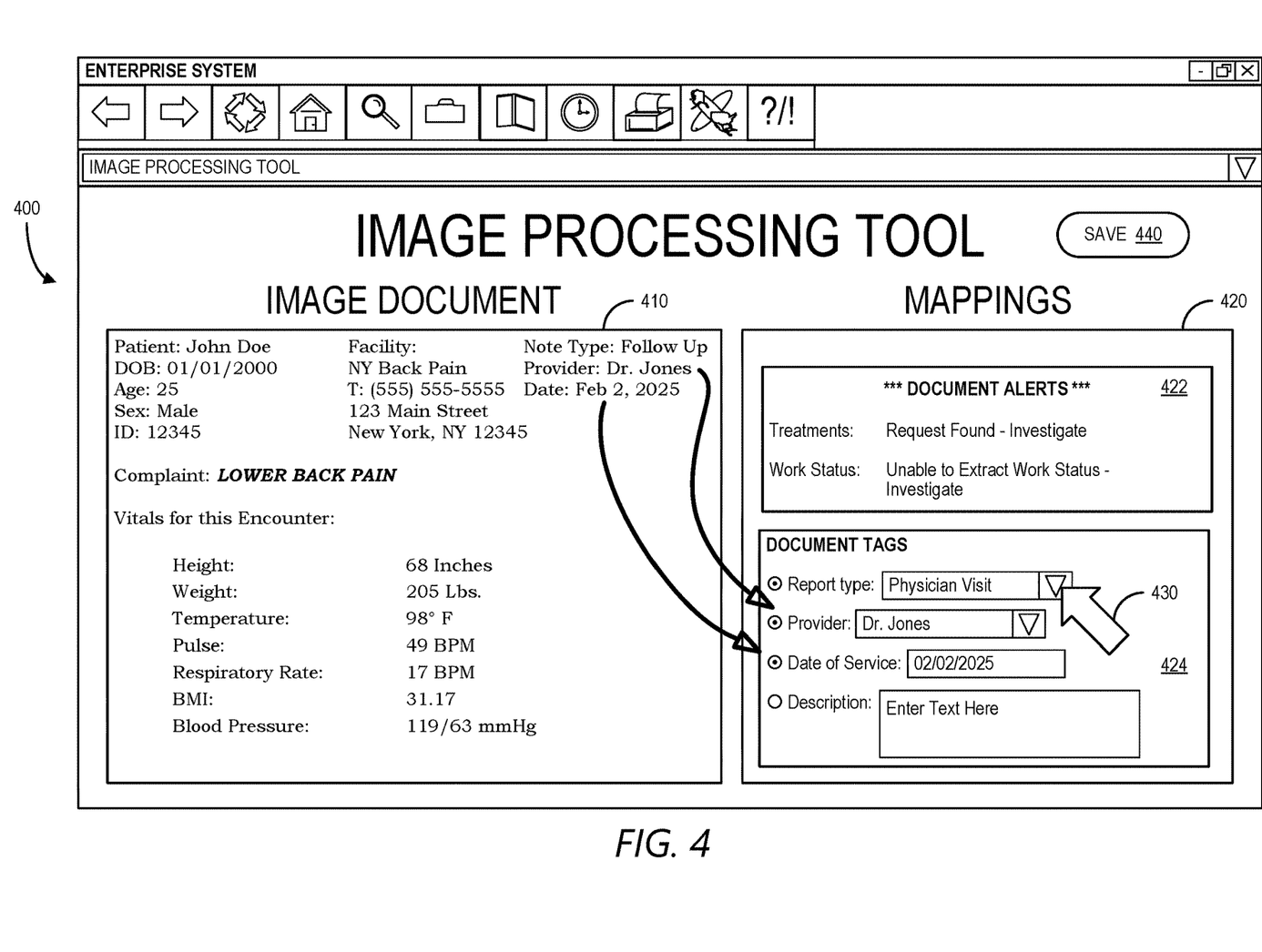
FIG. 4 is a medical record image display according to some embodiments.

For example, FIG. 4 is a medical record image display 400 according to some embodiments. The display 400 includes a rendering of the original image document 410 received by the system (e.g., a rendering of the PDF or BMP document file). Moreover, automatically generated mappings 420, based on cloud-generated OCR and NLP data, are also provided on the display 400. The mappings 420 might include document alerts 422 (e.g., when the system detects that information is missing or requires specific action by the user) and/or document tags 424 (e.g., pre-defined data fields associated with automated imaging processing). For example, the system might automatically map "Dr. Jones" as a medical provider and "02/02/2025" as a date of service (after converting the date from "Feb. 2, 2025") as illustrated by arrows in FIG. 4. A user may then adjust the mappings 420 as appropriate (e.g., via a touchscreen, keyboard, and/or computer mouse pointer 430) and select a "Save" icon 440 when the information is correct.

Figure 5:
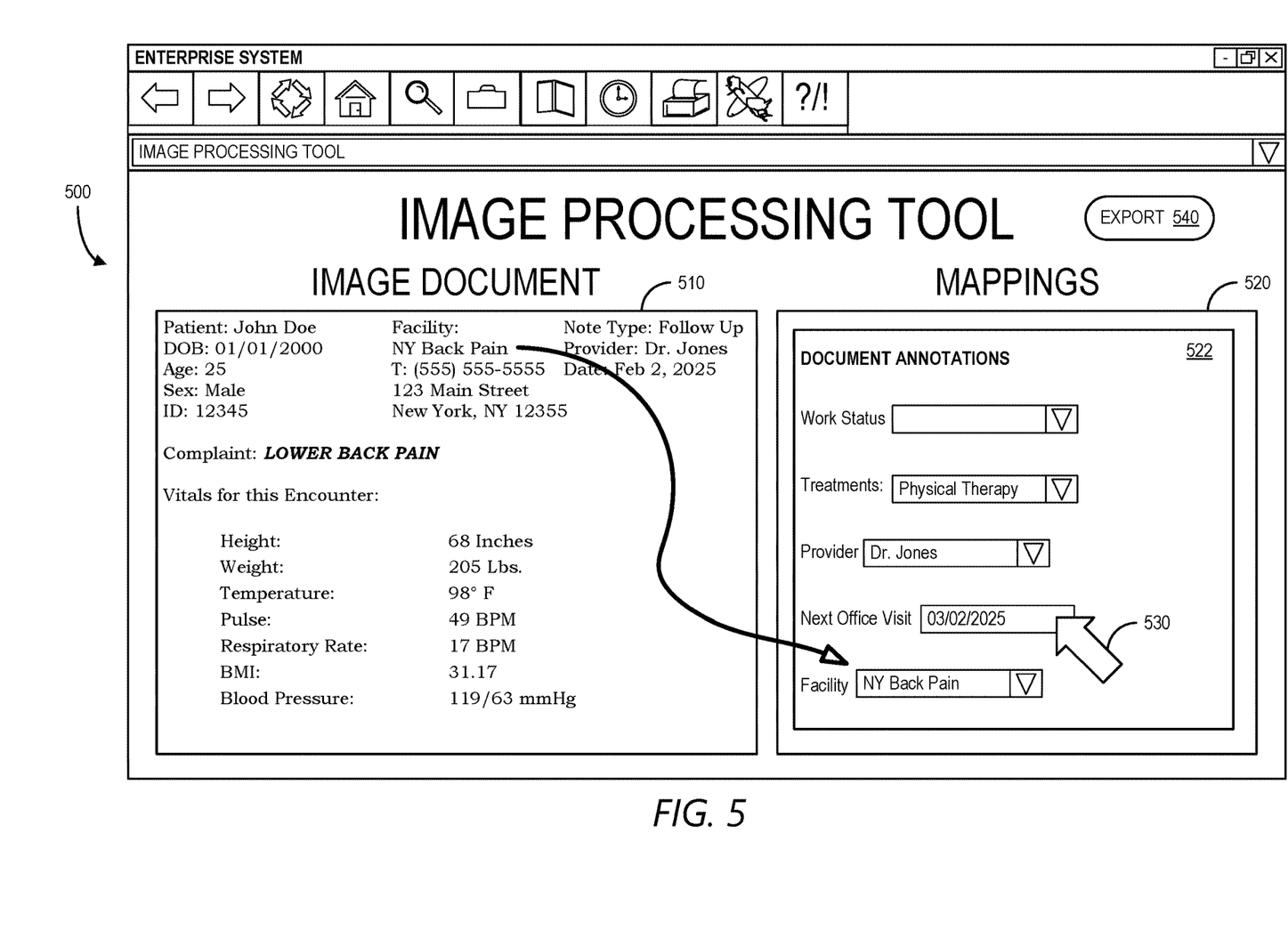
FIG. 5 is another medical record image display in accordance with some embodiments.

Note that other types of automatic mappings of information may also be supported by the system. FIG. 5 is another medical record image display 500 in accordance with some embodiments. As before, the display 500 includes a rendering of the original image document 510 received by the system along with automatically generated mappings 520 based on cloud-generated OCR and NLP data. The mappings 520 might include document annotations 522 (e.g., pre-defined document classifications). For example, the system might automatically map "NY Back Pain" as a medical treatment facility as illustrated by an arrow in FIG. 5. A user may then adjust the mappings 520 as appropriate (e.g., via a touchscreen, keyboard, and/or computer mouse pointer 530) and select an "Export" icon 540 when the information is correct.

Figure 6:
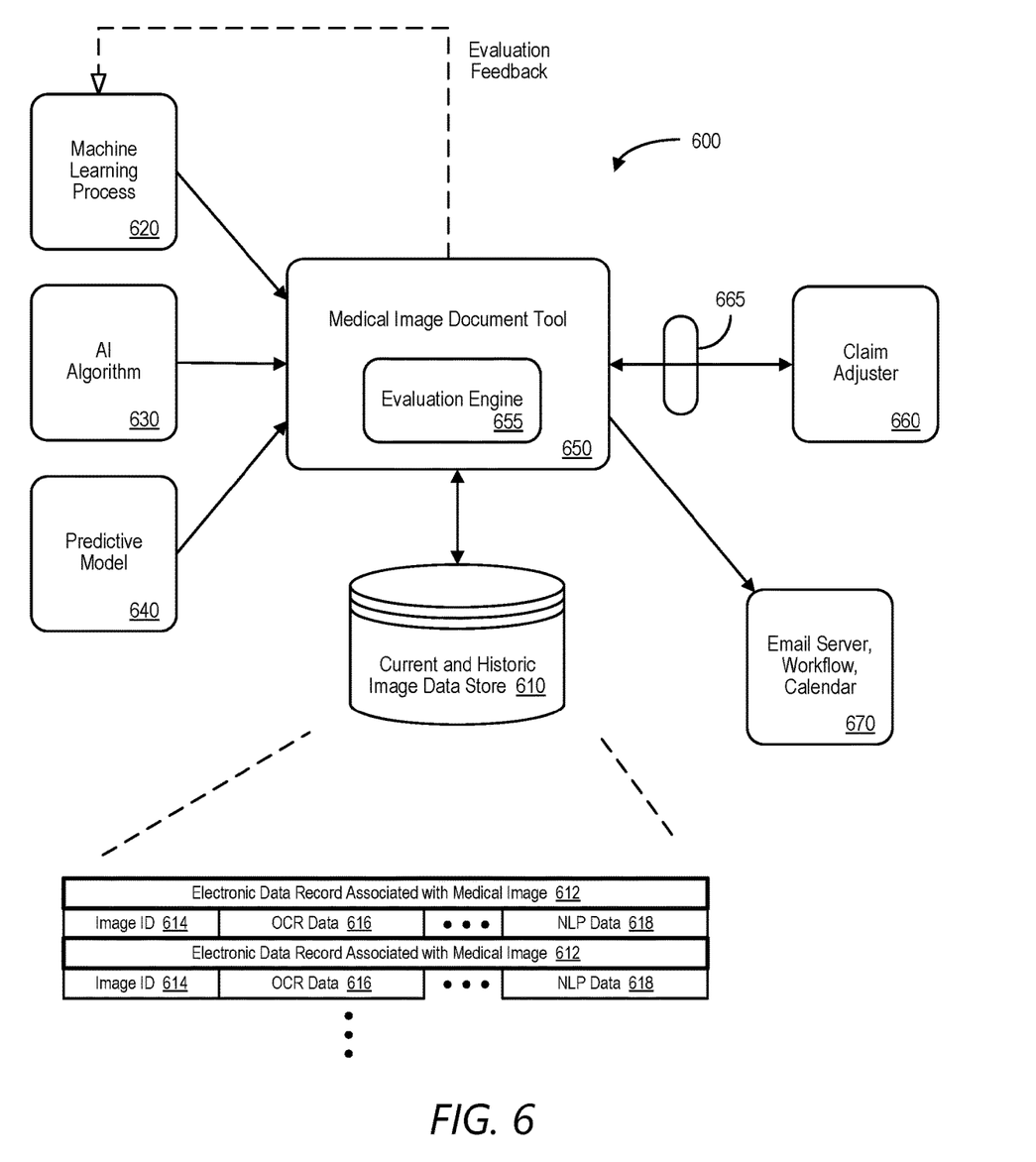
FIG. 6 is a more detailed system architecture according to some embodiments of the present invention.

FIG. 6 is a more detailed high-level block diagram of a system 600 in accordance with some embodiments. As before, the system 600 includes a medical image document tool 650 that may access information in a current and historic image data store 610. The medical image document tool 650 may also retrieve information from a machine learning process 620, an Artificial Intelligence ("AI") algorithm 630, and/or predictive models 640 in connection with an evaluation engine 655. The medical image document tool 650 may also exchange information with claim adjuster 660 (e.g., via communication port 665 that might include a firewall) to enable a manual review of automatically generated image tags. According to some embodiments, evaluation feedback is provided to the machine learning process 620 (e.g., so that an OCR and/or NLP process or workflow assignment can be automatically improved). The medical image document tool 650 might also transmit information directly to an email server (or postal mail server), a workflow application, and/or a calendar application 670 to facilitate image document management.

The medical image document tool 650 may store information into and/or retrieve information from the current and historic image data store 610. The current and historic image data store 610 might, for example, store electronic records 612 representing a plurality of medical image documents, each electronic record having a set of attribute values including an image identifier 614, OCR data 616, NLP data 618, etc. According to some embodiments, the system 600 may also provide a dashboard view of image document management information.

Figure 7:
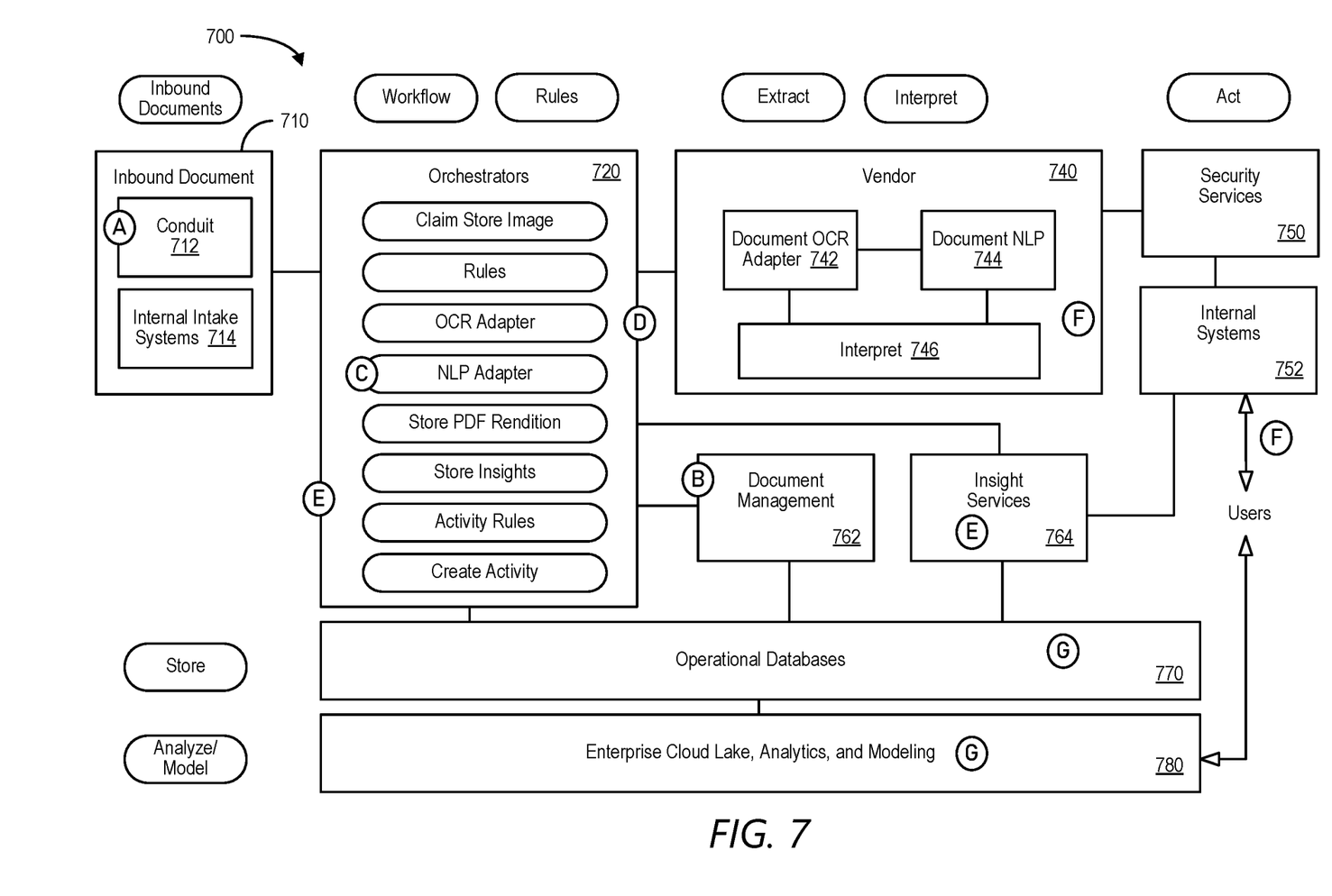
FIG. 7 is a medical record image management system in accordance with some embodiments.

FIG. 7 is a medical record image management system 700 in accordance with some embodiments. The system 700 might be associated with, for example, workers' compensation or property and casualty insurance. The system may receive an inbound document 710, such as medical record images, via a conduit 712 (e.g., email, postal mail, fax machine, etc.) and/or internal intake systems 714 (e.g., a user upload or a claim processing system). For example, at (A) an enterprise mail room vendor may receive paper mail, email, and fax documents. The vendor may then scan, index, and assign a document type to the documents (such as "medical record"). The original document may then be provided to orchestrators 720, such as via a composite XML file. The orchestrators 720 may include orchestrated steps, such as claim store image, rules, an OCR adapter, an NLP adapter, store PDF rendition, store insights, activity rules, create activity, etc. At (B), the document images may be stored in a document management repository 762.

At (C), based on rules for medical records, the orchestrators 720 make service call(s) including document image and document meta data to perform OCR and NLP related functions. In particular, a cloud-based computing vendor 740 may utilize a document OCR adapter 742 service call and/or document NLP 744 service call as well as enterprise-specific service calls. According to some embodiments, the vendor 740 may also interpret 746 the received information (e.g., in connection with concept rules, concept models, concept data, etc.). For example, after the OCR and NLP functions are executed, information may be returned to the orchestrators 720 by the vendor 740 at (D), such as document data, TXT files, searchable PDF, JSON, HTML, zip files, and/or XML renditions of the image.

At (E), the orchestrators 720 may update data repositories via insight services 764 and make service calls to a Line Of Business ("LOB") claim administration system (e.g., internal enterprise systems 752) to update data, perform automated decisions, call rules to suppress activities, etc. as needed and create workflow activities. According to some embodiments, security services 750 may include an enterprise directory and/or a LOB authorization service to prevent unauthorized access to information. At (F), users (e.g., claim handlers) may access information via the internal systems 752 to process claims and/or utilize decision automation services. For example, data from a JSON file of the document may be used for validation of concepts and an annotation User Interface ("UI") may provide a searchable PDF (with concepts displayed and highlighted) based on information extracted during NLP via the insight services 764. After an update, the orchestrators call services to perform automated decisions and/or recommendations.

At (G), operational databases 770 (e.g., associated with an orchestration database, a claim database, a Network Attached Storage ("NAS") file store, an Operational Data Store ("ODS") database, etc.) and/or enterprise cloud lake, analytics, and modeling 780 (e.g., associated with an enterprise unstructured data lake, a text factory, a claim data warehouse, claim tables, etc.) may be updated. In this way, users (such as data science or Information Technology ("IT") support users) may produce insights and/or models based on the inbound image documents 710. For example, all of the data needed for operational medical claim processing may be contained in an ODS (or available via services) in substantially real-time.

Figure 8:
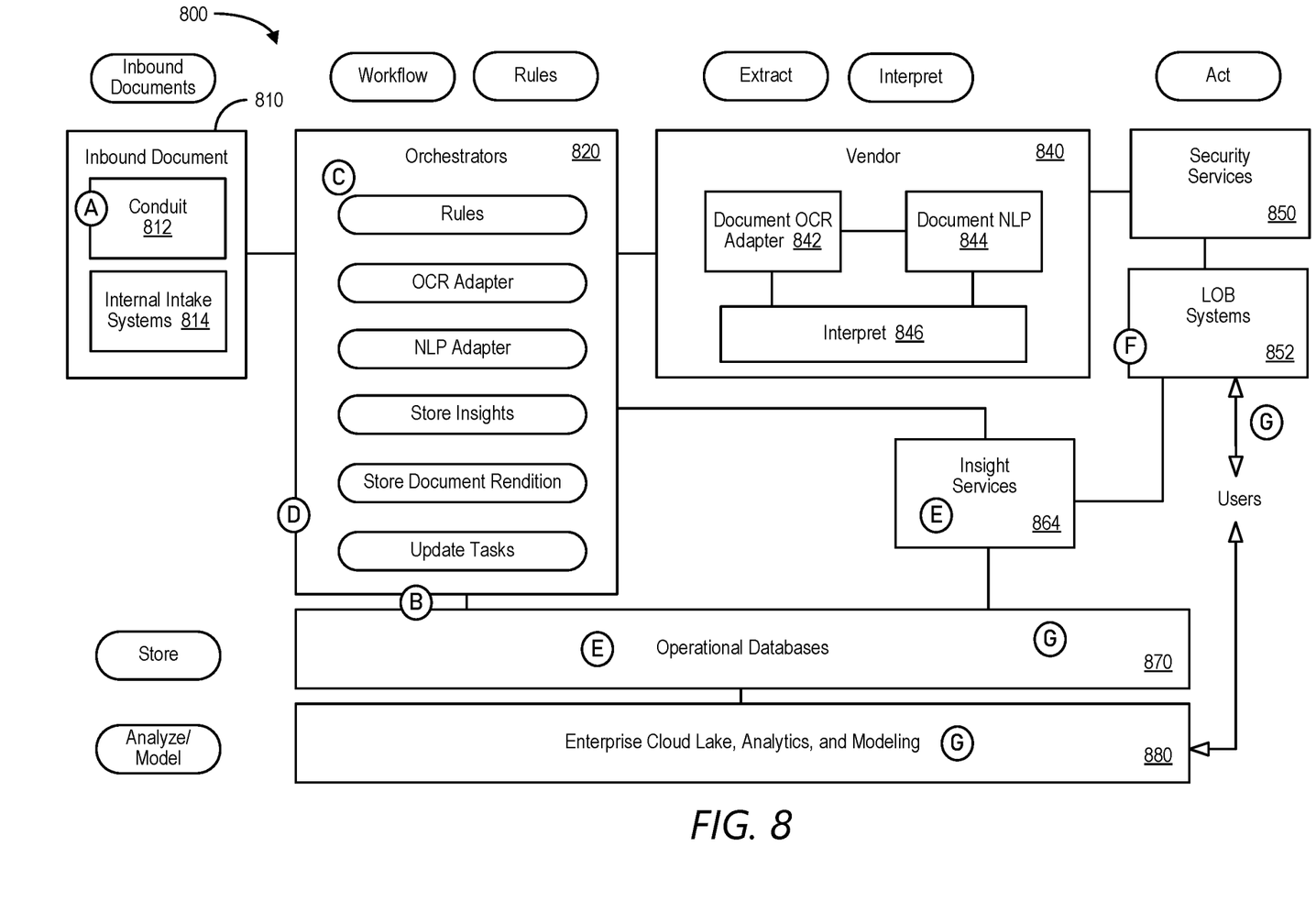
FIG. 8 is another medical record image management system according to some embodiments.

FIG. 8 is another medical record image management system 800 according to some embodiments. The system 800 might be associated with, for example, group benefits insurance. As before, the system may receive an inbound document 810, such as medical record images, via a conduit 812 (e.g., email, postal mail, fax machine, etc.) and/or internal intake systems 814 (e.g., a user upload or an attending physician's statement). For example, at (A) a mail room vendor may receive paper mail, email, and fax documents. The vendor may then scan the documents and a workflow might allow for document typing, indexing and creating new workflow tasks within the correct claim file for the document. At (B), an application API may store documents and/or searchable PDFs in operational databases 870 (e.g., in connection with a document management repository associated with the created task. Orchestrators 820 may be associated with enterprise rules or logic, an OCR adapter, an NLP adapter, insight storage, document rendition storage, and task updates.

At (C), an orchestrator, based on rules for medical records, may make service call(s) including document image and document meta data to perform OCR and NLP related functions. For example, a cloud-based computing vendor 840 may use document OCR adapter 842 service calls and/or document NLP 844 service calls as well as enterprise-specific service calls. According to some embodiments, the vendor 840 may also interpret 846 the received information (e.g., in connection with concept rules, concept models, transformations, etc.). For example, after the OCR and NLP functions are executed, information may be returned to the orchestrators 820 by the vendor 840, such as document data, TXT files, searchable PDF, JSON, HTML, zip files, and/or XML renditions of the image at (D). The initial Representational State Transfer ("REST") call might send the image and the return a JSON that contains a unique identifier for the OCR/NLP transaction. The orchestrators 820 may poll or subscribe looking for the unique identifier which will indicate a finished state and then execute a call to retrieve an OCR/NLP result set.

At (E), the orchestrators 820 may update the operational databases 870 (e.g., associated with an NAS file store, an ODS database, etc.) and/or enterprise cloud lake, analytics, and modeling 880 (e.g., associated with a text factory, an enterprise unstructured data lake, a claim data warehouse, claim tables, etc.) may be updated. In this way, users (such as data science or IT support users) may produce insights via insight services 864 and/or models based on the inbound image documents 810. The orchestrators 820 may also update task data to perform automated decisions.

At (F), data from the JSON of the document may be used for validation of concepts, as part of a task, extracted during NLP. After validation of concepts, service calls to perform automated decisions and/or recommendations may run and present recommendations via LOB systems 852 and/or security services 850. According to some embodiments, the security services 850 include an enterprise directory and/or a LOB authorization service to prevent unauthorized access to information. At (G), users such as claim handlers may access all of the data needed for operational medical claim processing (which is contained in the operational database or available via services) in substantially real-time.

Figure 9:
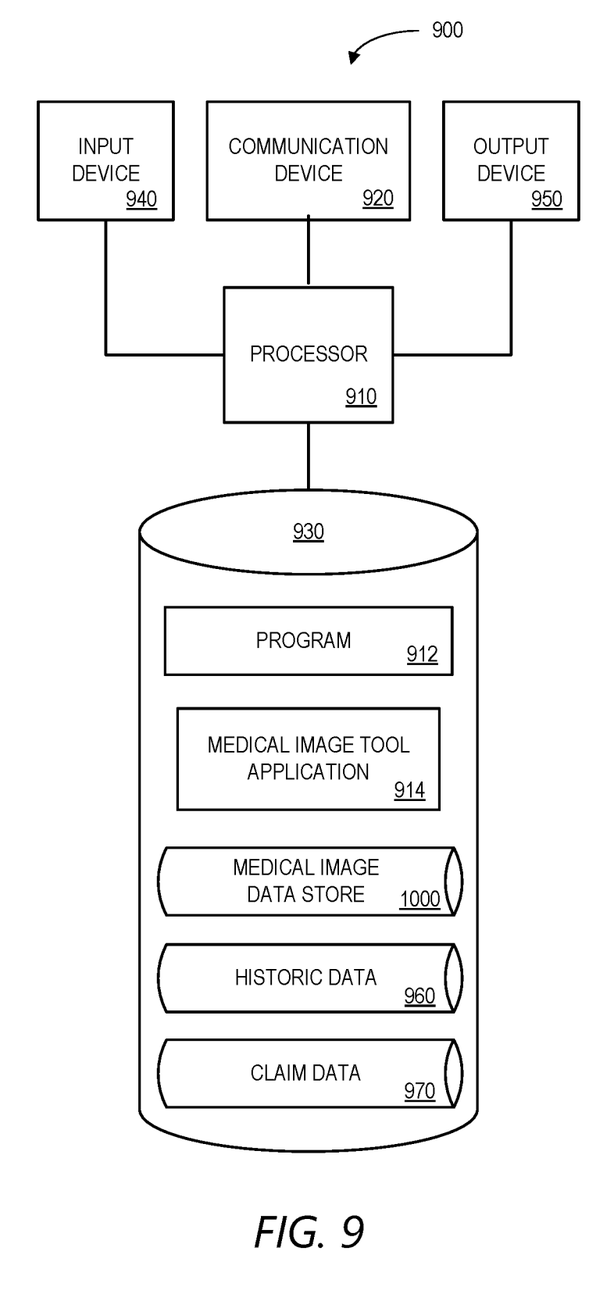
FIG. 9 is a block diagram of an apparatus or platform in accordance with some embodiments of the present invention.

The embodiments described herein may be implemented using any number of different hardware configurations. For example, FIG. 9 illustrates an apparatus or platform 900 that may be, for example, associated with the systems 100, 600 of FIGS. 1 and 6, respectively (or any other system described herein). The platform 900 comprises a processor 910, such as one or more commercially available Central Processing Units ("CPUs") in the form of one-chip or multi-chip microprocessors, coupled to a communication device 920 configured to communicate via a communication network (not shown in FIG. 9). The communication device 920 may be used to communicate, for example, with one or more remote devices. The platform 900 further includes an input device 940 (e.g., a mouse and/or keyboard to enter image information) and an output device 950 (e.g., a computer monitor to display automatically generated image tags, document annotations, alerts, etc.).

The processor 910 also communicates with a storage device 930. The storage device 930 may comprise any appropriate information storage device, including combinations of magnetic storage devices (e.g., a hard disk drive), optical storage devices, mobile telephones, and/or semiconductor memory devices. The storage device 930 stores a program 912 and/or a medical image tool application 914 for controlling the processor 910. The processor 910 performs instructions of the programs 912, 914, and thereby operates in accordance with any of the embodiments described herein. For example, the processor 910 may receive, from a remote user device, an indication of a selected image document. The processor 910 may then retrieve information about the selected image document and automatically map at least some of the associated optical character recognition and natural language processing information to pre-determined document data fields. The processor 910 may display the mapped information and receive an indication of acceptance. The mapped information and image file may then be stored, and a workflow may be automatically assigned to the selected image document in accordance with the mapped information and enterprise logic. The workflow might indicate, for example, that no further manual review of an insurance claim is required.

The programs 912, 914 may be stored in a compressed, uncompiled and/or encrypted format. The programs 912, 914 may furthermore include other program elements, such as an operating system, a data store management system, and/or device drivers used by the processor 910 to interface with peripheral devices.

As used herein, information may be "received" by or "transmitted" to, for example: (i) the platform 900 from another device; or (ii) a software application or module within the platform 900 from another software application, module, or any other source.

In some embodiments (such as shown in FIG. 9), the storage device 930 stores historic data 960 (e.g., to evaluate tag generation and/or workflow assignments over time to train an AI algorithm), claim data 970, and a medical image data store 1000. An example of a data store that may be used in connection with the platform 900 will now be described in detail with respect to FIG. 10. Note that the data store described herein is only one example, and additional and/or different information may be stored therein. Moreover, various data stores might be split or combined in accordance with any of the embodiments described herein.

Figure 10:
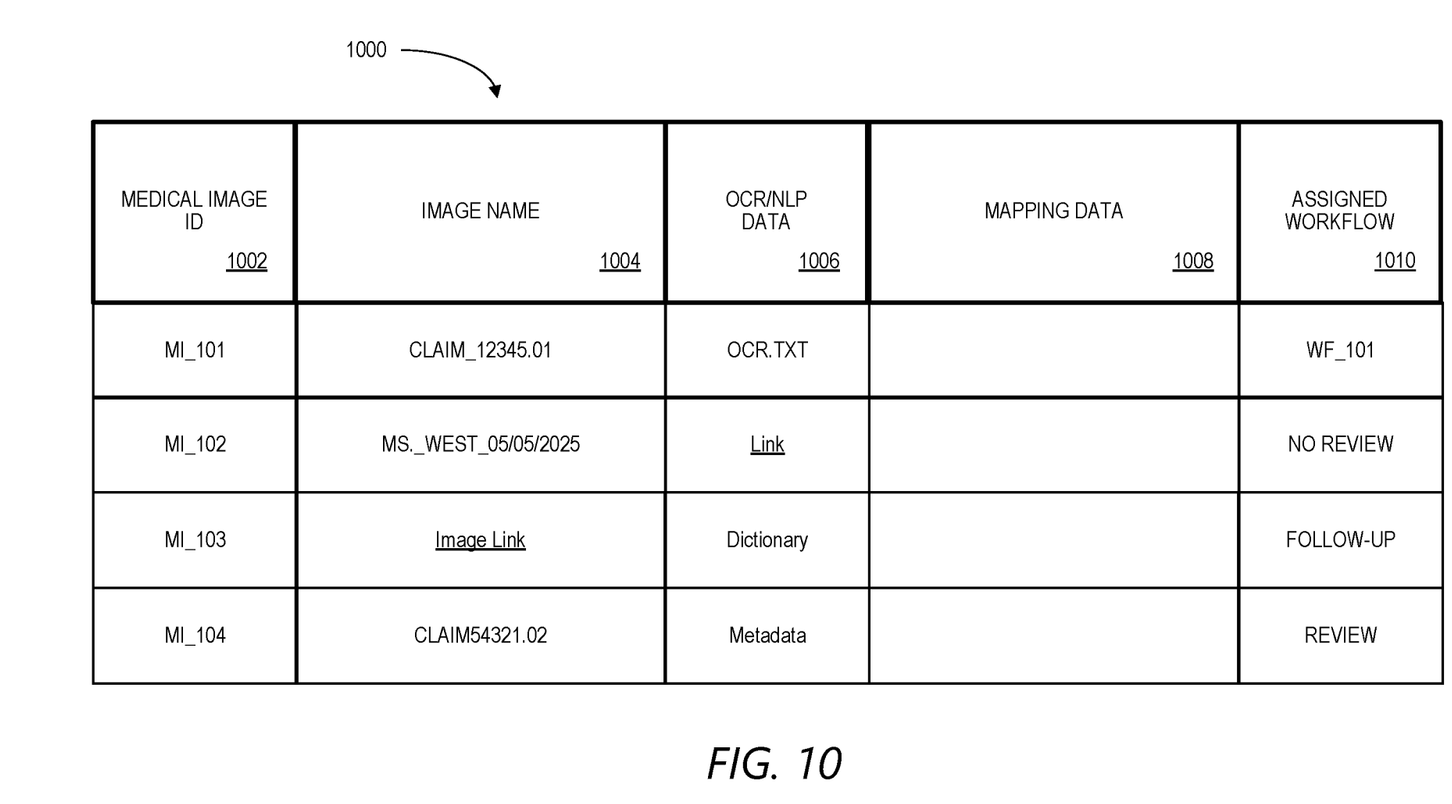
FIG. 10 is a tabular portion of an image document data store according to some embodiments.

Referring to FIG. 10, a table is shown that represents the medical image data store 1000 that may be stored at the platform 900 according to some embodiments. The table may include, for example, entries identifying incoming medical images that are being processed. The table may also define fields 1002, 1004, 1006, 1008, 1010 for each of the entries. The fields 1002, 1004, 1006, 1008, 1010, may, according to some embodiments, specify: a medical image identifier 1002, an image name 1004, OCR and NLP data 1006, mapping data 1008, and an assigned workflow 1010.

The information in the medical image data store 1000 may be created and updated, for example, based on information received from cloud computing environment.

The medical image identifier 1002 and image name 1004 may be, for example, unique alphanumeric codes identifying an inbound image document (e.g., a doctor's report, a hospital invoice, physician notes, etc.). The OCR and NLP data 1006 may represent information (e.g., a JSON file) containing data that has been automatically extracted from the image via a cloud computing environment. The mapping data 1008 may represent, for example, image tags, document annotations, alerts, etc. that are automatically created based on the OCR and NLP data 1006 and enterprise logic. The assigned workflow 1010 might comprise, for example, an automatically assigned series of actions or tasks that are to be performed in connection with the medical image (e.g., in some cases, the image might require further review or follow-up to gather more information while in other cases no further action may be needed).

Thus, some embodiments may provide improved image document monitoring, evaluation, and scoring. The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Figure 11:
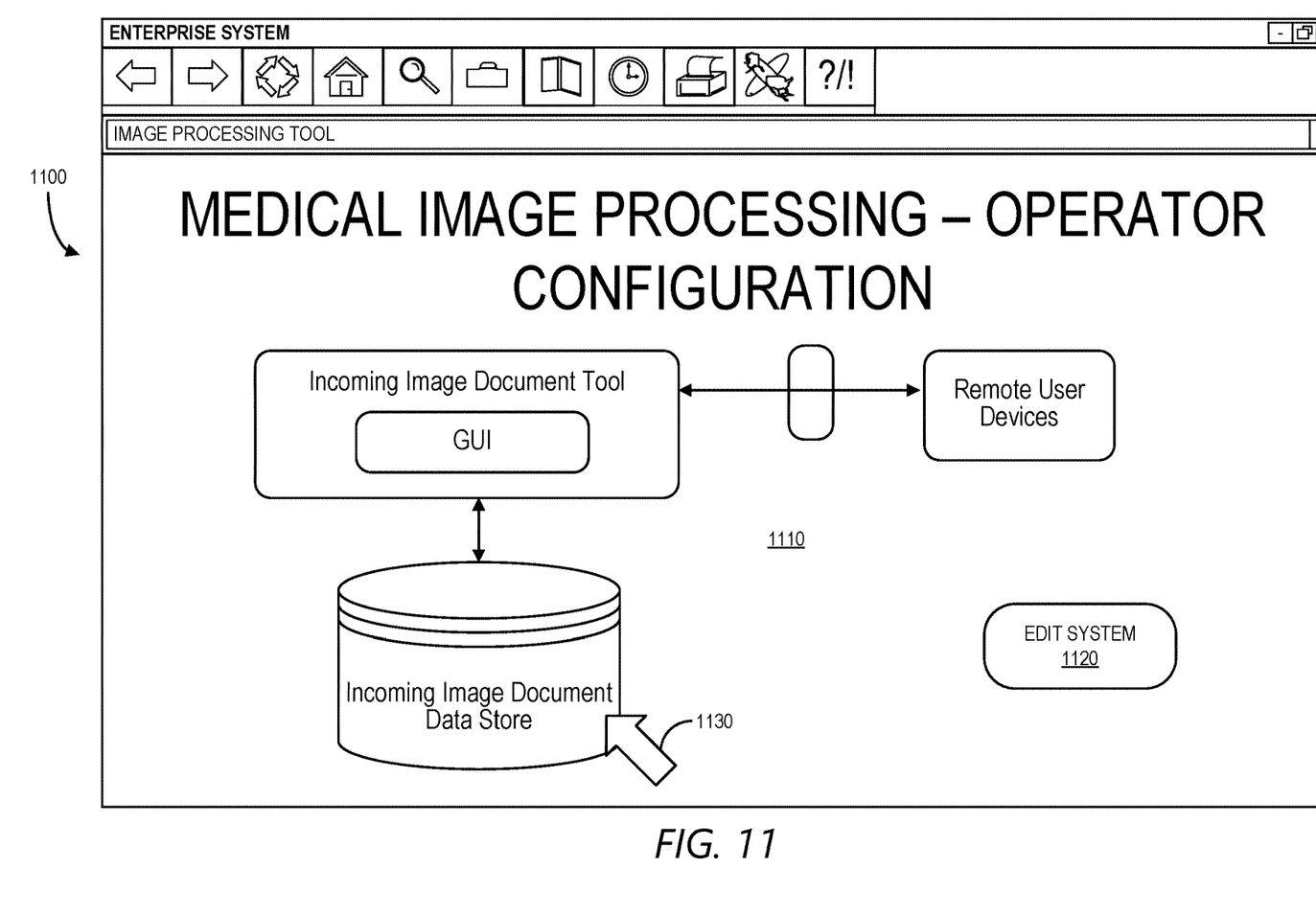
FIG. 11 is an operator or administrator display in according to some embodiments.
Figure 12:
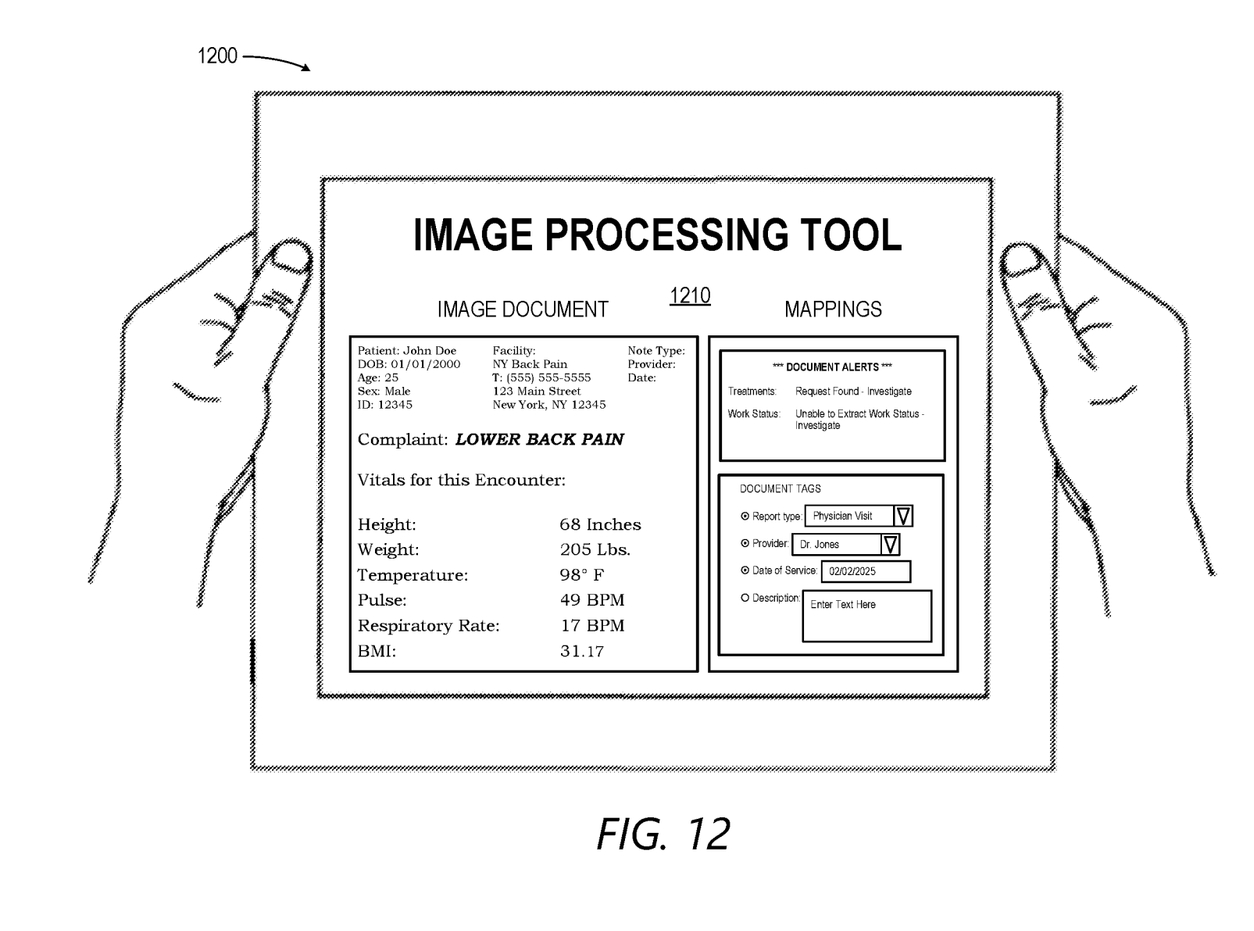
FIG. 12 illustrates a handheld tablet according to some embodiments described herein.

Although specific hardware and data configurations have been described herein, note that any number of other configurations may be provided in accordance with embodiments of the present invention (e.g., some of the information associated with the data stores described herein may be combined or stored in external systems). Note that the displays and devices illustrated herein are only provided as examples, and embodiments may be associated with any other types of interfaces. For example, FIG. 11 is an administrator or operator display 1100 including graphical representations of elements 1110 of an image processing system. Selection of a portion or element of the display 1100 might result in the presentation of additional information about that portion or device (e.g., a popup window presenting a more detailed view of data mappings, communication addresses for remote devices, or other specifics of the system implementation) or let an operator or administrator enter or annotate additional information about the image system (e.g., based on recommendations from an ML model). Selection of an "Edit System" icon 1120 (e.g., by touchscreen or computer mouse pointer 1130) might cause the system or platform to save changes, transmit insurance claim information to another party, etc. According to some embodiments a warning signal or alert may be automatically transmitted to a communication device (e.g., associated with a claim handler) when a document value moves beyond a threshold (e.g., when a risk or volatility score associated with a medical image or insurance claim file exceeds a pre-determined limit). Similarly, FIG. 12 illustrates a handheld tablet 1200 display 1210 in accordance with some embodiments. The display 1210 includes a graphical representation of a received medical image and some automatic tagging suggestions. Although medical images are used herein as one example of a document processing system, note that embodiments might be associated with any other types of images (e.g., financial images, educational images, invoices, purchase order, etc.).

The present invention has been described in terms of several embodiments solely for the purpose of illustration. Persons skilled in the art will recognize from this description that the invention is not limited to the embodiments described but may be practiced with modifications and alterations limited only by the spirit and scope of the appended claims.

What is claimed:

1. A system to facilitate image document processing for an enterprise, comprising:
   (a) an incoming image document data store containing electronic records, each record including an image document identifier and an image file along with associated optical character recognition and natural language processing information generated by a cloud-based computing environment for the enterprise;
   (b) an incoming image document tool, coupled to the incoming image document data store, including:
      a computer processor for executing program instructions; and
      a memory, coupled to the computer processor, storing program instructions that, when executed by the computer processor, cause the incoming image document tool to:
         (i) receive, from a user of a remote user device via a distributed communication network, an indication of a selected image document,
         (ii) retrieve, from the incoming image document data store, information about the selected image document,
         (iii) based on the retrieved information, automatically map at least some of the associated optical character recognition and natural language processing information for the selected image document to pre-determined document data fields,
         (iv) display the mapped information via the remote user device, the display including a population of the pre-determined document data fields with corresponding optical character recognition and natural language processing information for the selected image document,
         (v) receive, from the remote user device, an indication of acceptance of the mapped information,
         (vi) responsive to the received indication of acceptance, store the mapped information and image file in an enterprise data store, and
         (vii) automatically assign a workflow to the selected image document in accordance with the mapped information and enterprise logic; and
   (c) a communication port coupled to the incoming image document tool to facilitate a transmission of data with the remote user device to provide a graphical interactive user interface display via the distributed communication network, the graphical interactive user interface including an indication of the assigned workflow.

2. The system of claim 1, wherein the indication of acceptance of the mapped information includes in some cases at least one adjustment to the mapped information.

3. The system of claim 1, wherein the indication of acceptance of the mapped information includes in some cases no adjustment to the mapped information.

4. The system of claim 1, wherein the incoming image files comprise medical records.

5. The system of claim 4, wherein the medical records are received via at least on of: (i) electronic mail, (ii) a facsimile machine, and (iii) a scanner device.

6. The system of claim 3, wherein the enterprise comprises an insurer and the assigned workflow is associated with insurance claim processing.

7. The system of claim 5, wherein the enterprise logic is associated with at least one of: (i) a risk score, (ii) a volatility score, (iii) a predicted recovery time.

8. The system of claim 6, wherein the insurance claim processing is associated with one of: (i) workers' compensation insurance, (ii) group benefit insurance, (iii) short term disability insurance, (iv) long term disability insurance, (v) automobile insurance, and (vi) general liability insurance.

9. The system of claim 3, wherein the pre-determined document data fields include at least one of: (i) an insurance policy identifier, (ii) a patient name, (iii) a patient date of birth, (iv) a medical provider identifier, (v) an injury description, (vi) a medical treatment date, (vii) medical treatment information, (viii) an insurance claim identifier, and (ix) claim demographic information.

10. The system of claim 1, wherein the mapped information is further processed by at least one of: (i) a Machine Learning ("ML") model, (ii) an automated data analysis algorithm, and (iii) a symbolic rules model.

11. The system of claim 1, wherein the associated optical character recognition and natural language processing information is represented by a JavaScript Object Notation ("JSON") file.

12. A computer-implemented method to facilitate image document processing for an enterprise, comprising:
   receiving, by a computer processor of an incoming image document tool from a user of a remote user device via a distributed communication network, an indication of a selected image document;
   retrieving, from an incoming image document data store, information about the selected image document, wherein the incoming image document data store contains electronic records, each record including an image document identifier and an image file along with associated optical character recognition and natural language processing information generated by a cloud-based computing environment for the enterprise;
   based on the retrieved information, automatically mapping at least some of the associated optical character recognition and natural language processing information for the selected image document to pre-determined document data fields;
   displaying the mapped information via the remote user device, the display including a population of the pre-determined document data fields with corresponding optical character recognition and natural language processing information for the selected image document;
   receiving, from the remote user device, an indication of acceptance of the mapped information;
   responsive to the received indication of acceptance, storing the mapped information and image file in an enterprise data store; and
   automatically assigning a workflow to the selected image document in accordance with the mapped information and enterprise logic.

13. The method of claim 12, wherein the incoming image files comprise medical records.

14. The method of claim 13, wherein the medical records are received via at least on of: (i) electronic mail, (ii) a facsimile machine, and (iii) a scanner device.

15. The method of claim 13, wherein the enterprise comprises an insurer and the assigned workflow is associated with insurance claim processing.

16. The method of claim 15, wherein the enterprise logic is associated with at least one of: (i) a risk score, (ii) a volatility score, (iii) a predicted recovery time.

17. The method of claim 16, wherein the insurance claim processing is associated with one of: (i) workers' compensation insurance, (ii) group benefit insurance, (iii) short term disability insurance, (iv) long term disability insurance, (v) automobile insurance, and (vi) general liability insurance.

18. The method of claim 13, wherein the pre-determined document data fields include at least one of: (i) an insurance policy identifier, (ii) a patient name, (iii) a patient date of birth, (iv) a medical provider identifier, (v) an injury description, (vi) a medical treatment date, (vii) medical treatment information, (viii) an insurance claim identifier, and (ix) claim demographic information.

19. A non-transitory computer-readable medium storing instructions adapted to be executed by a computer processor to perform a method to facilitate image document processing for an enterprise, the method comprising:

receiving, by a computer processor of an incoming image document tool from a user of a remote user device via a distributed communication network, an indication of a selected image document;

retrieving, from an incoming image document data store, information about the selected image document, wherein the incoming image document data store contains electronic records, each record including an image document identifier and an image file along with associated optical character recognition and natural language processing information generated by a cloud-based computing environment for the enterprise;

based on the retrieved information, automatically mapping at least some of the associated optical character recognition and natural language processing information for the selected image document to pre-determined document data fields;

displaying the mapped information via the remote user device, the display including a population of the pre-determined document data fields with corresponding optical character recognition and natural language processing information for the selected image document;

receiving, from the remote user device, an indication of acceptance of the mapped information;

responsive to the received indication of acceptance, storing the mapped information and image file in an enterprise data store; and automatically assigning a workflow to the selected image document in accordance with the mapped information and enterprise logic.

20. The medium of claim 19, wherein the mapped information is further processed by at least one of: (i) a Machine Learning ("ML") model, (ii) an automated data analysis algorithm, and (iii) a symbolic rules model.

21. The medium of claim 19, wherein the associated optical character recognition and natural language processing information is represented by a JavaScript Object Notation ("JSON") file.

* * * * *